(12) United States Patent
Lieberman et al.

(10) Patent No.: US 12,133,933 B2
(45) Date of Patent: Nov. 5, 2024

(54) GROWTH FACTOR TRANSDUCED CELL-LOADED CERAMIC SCAFFOLD FOR BONE REGENERATION AND REPAIR

(71) Applicant: UNIVERSITY OF SOUTHERN CALIFORNIA, Los Angeles, CA (US)

(72) Inventors: Jay R. Lieberman, Los Angeles, CA (US); William Pannell, Los Angeles, CA (US); Yong Chen, Los Angeles, CA (US); Xuan Song, Los Angeles, CA (US); Sofia Bougioukli, Los Angeles, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 458 days.

(21) Appl. No.: 16/899,363

(22) Filed: Jun. 11, 2020

(65) Prior Publication Data

US 2020/0316258 A1      Oct. 8, 2020

Related U.S. Application Data

(63) Continuation-in-part of application No. 16/337,893, filed as application No. PCT/US2017/054609 on Sep. 29, 2017.

(Continued)

(51) Int. Cl.

| A61L 27/38 | (2006.01) |
|---|---|
| A61L 27/10 | (2006.01) |
| A61L 27/12 | (2006.01) |
| A61L 27/22 | (2006.01) |
| A61L 27/54 | (2006.01) |
| B28B 1/00 | (2006.01) |
| B29C 64/379 | (2017.01) |

(Continued)

(52) U.S. Cl.
CPC ............ *A61L 27/3847* (2013.01); *A61L 27/10* (2013.01); *A61L 27/12* (2013.01); *A61L 27/227* (2013.01); *A61L 27/3821* (2013.01);

*A61L 27/3834* (2013.01); *A61L 27/54* (2013.01); *B28B 1/001* (2013.01); *B29C 64/379* (2017.08);

(Continued)

(58) Field of Classification Search
CPC ............... A61L 27/227; A61L 27/3821; A61L 27/3834; A61L 27/54; A61L 2300/414; A61L 2430/02; B33Y 10/00
See application file for complete search history.

(56) References Cited

U.S. PATENT DOCUMENTS

| 6,077,987 A | 6/2000 | Breitbart et al. |
|---|---|---|
| 6,730,252 B1 * | 5/2004 | Teoh ...................... A61L 27/18 264/234 |

(Continued)

FOREIGN PATENT DOCUMENTS

| EP | 2667809 B1 * | 11/2015 | ......... A61B 17/8076 |
|---|---|---|---|
| WO | WO-2018064631 A1 * | 4/2018 | ............... A61F 2/28 |

OTHER PUBLICATIONS

Bougioukli et al. "In vitro evaluation of a lentiviral two-step transcriptional amplification system using GAL4FF transactivator for gene therapy applications in bone repair", Gene Therapy (2018) 25:260-268. (Year: 2018).*

(Continued)

*Primary Examiner* — Carlos A Azpuru
*Assistant Examiner* — Casey S Hagopian
(74) *Attorney, Agent, or Firm* — Snell & Wilmer LLP

(57) ABSTRACT

Disclosed herein are methods of regional gene-therapy with growth-factor transduced cells, in bone graft scenarios. In embodiments, the methods comprise use of 3D printed scaffolds.

8 Claims, 14 Drawing Sheets

FIG. 6

Related U.S. Application Data

(60) Provisional application No. 62/401,745, filed on Sep. 29, 2016.

(51) Int. Cl.
   *B29K 509/02*    (2006.01)
   *B29L 31/00*     (2006.01)
   *B33Y 10/00*     (2015.01)
   *B33Y 40/20*     (2020.01)
   *B33Y 70/00*     (2020.01)
   *B33Y 80/00*     (2015.01)
   *B29C 64/129*    (2017.01)

(52) U.S. Cl.
   CPC ............... *B33Y 40/20* (2020.01); *B33Y 70/00* (2014.12); *B33Y 80/00* (2014.12); *A61L 2300/414* (2013.01); *A61L 2430/02* (2013.01); *B29C 64/129* (2017.08); *B29K 2509/02* (2013.01); *B29L 2031/7532* (2013.01); *B33Y 10/00* (2014.12)

(56) References Cited

U.S. PATENT DOCUMENTS

| | | | |
|---|---|---|---|
| 2004/0007809 A1 | 4/2004 | Binette et al. | |
| 2014/0017834 A1 | 6/2014 | Byrne et al. | |
| 2014/0178346 A1* | 6/2014 | Byrne | A61K 38/1875 424/93.21 |
| 2015/0150681 A1* | 6/2015 | Ricci | A61F 2/2875 264/340 |
| 2020/0022816 A1 | 1/2020 | Lieberman et al. | |

OTHER PUBLICATIONS

"Bone Plate Definition", Spine-health, accessed online on Apr. 11, 2023 at <https://www.spine-health.com/glossary/bone-plate#:~:text=A%20bone%20plate%20is%20a,dislodgement%20of%20the%20bone%20graft.>. (Year: 2023).*

International Search Report and Written Opinion dated Dec. 14, 2017 for Corresponding International PCT Patent Application No. PCT/US2017/054609.

International Preliminary Report on Patentability dated Apr. 2, 2019 in Application No. PCT/US2017/054609.

Trombetta et al., "3D Printing of Calcium Phosphate Ceramics for Bone Tissue Engineering and Drug Delivery" Annals of Biomedical Engineering, vol. 45 Issue 1; pp. 23-44 (2016).

Li et al. "Macroporous Biphasic Calcium Phosphate Scaffold with High-Permeability/Prosity Ratio" Tissue Engineering, vol. 9 Issue 3; pp. 535-548 (2004).

Wilson et al., "Design and fabrication of standardized hydroxyapatite scaffolds with a defined macro-architecture by rapid prototyping for bone-tissue-engineering research" Journal of Biomedical Materials Research, vol. 68A Issue 1; pp. 123-132 (2004).

* cited by examiner

GROWTH FACTOR TRANSDUCED CELL-LOADED CERAMIC SCAFFOLD FOR BONE REGENERATION AND REPAIR

CROSS-REFERENCE TO RELATED APPLICATIONS

This application is a continuation-in-part of U.S. patent application Ser. No. 16/337,893, filed on Mar. 28, 2019 entitled "GROWTH FACTOR TRANSDUCED CELL-LOADED CERAMIC SCAFFOLD FOR BONE REGENERATION AND REPAIR", which is a national phase (371) application of International Application PCT/US2017/054609 filed on Sep. 29, 2017 entitled "GROWTH FACTOR TRANSDUCED CELL-LOADED CERAMIC SCAFFOLD FOR BONE REGENERATION AND REPAIR", which claims the benefit and priority of U.S. provisional patent application Ser. No. 62/401,745, filed Sep. 29, 2016, the disclosures of each of which are incorporated herein in their entirety by reference.

GOVERNMENT LICENSE RIGHTS

This invention was made with government support under Grant No. 1335476 awarded by the National Science Foundation (NSF) and under Grant No. AR057076 awarded by the National Institutes of Health (NIH). The government has certain rights in the invention.

FIELD

The present disclosure relates to methods and apparatus for repairing bone tissue, and more particularly to combined use of custom 3D-printed calcium phosphate scaffolds and regional gene therapy in bone graft scenarios to heal critically sized bone defects.

BACKGROUND

Fracture non-union and inadequate bone formation in settings such as trauma, tumor, joint replacement and limb reconstructive surgeries are among the most challenging problems in orthopedic surgery. Autologous bone graft is the gold standard to use in such situations, but its disadvantage is limited availability of the graft and complications and pain associated with graft harvest. Researchers have explored the option of using precursor cells (from bone marrow, fat, muscle or other tissues) that have potential to transform into bone forming cells, but the methods to purify these cells and potential of these cells to form bone are limited unless stimulated by the growth factors. Regional gene therapy is an attractive option as it potentially allows the investigator to incorporate the desired gene encoding the growth factor essential for bone formation into the host cells and implant these cells back into the host at a particular site where they induce new bone formation.

Prior research has reported on the effect of regional gene therapy with bone morphogenetic protein-2-producing bone marrow cells on the repair of bone defects in rats, showing promise as one aspect of bone replacement therapy. "3D printing" broadly understood as additive manufacturing, has been proposed for forming scaffolds of calcium phosphate and collagen for bone regeneration, but not in conjunction with regional gene therapy. Additive manufacturing provides the advantage of custom shaping for individual bone replacement therapy, but its suitability in conjunction with regional gene therapy is poorly understood, if at all.

Bone regeneration in vivo or in vitro is desirable for providing more rapid and more effective clinical outcomes for treatment of severe bone injury. It would be desirable, therefore, to provide more effective methods and apparatus for bone regeneration and replacement of lost bone tissue.

SUMMARY

This summary and the following detailed description should be interpreted as complementary parts of an integrated disclosure, which parts may include redundant subject matter and/or supplemental subject matter.

In an aspect, a method for repairing a bone defect of a patient is provided, comprising providing a ceramic scaffold configured for filling the bone defect, loading the scaffold with growth factor transduced cells incorporating a gene that encodes a growth factor essential for bone formation, placing the ceramic scaffold with the growth factor transduced cells in or across the bone defect, and stabilizing the ceramic scaffold with the growth factor transduced cells in the patient until the bone defect is healed.

In an aspect, a method of repairing a bone defect of a patient is provided, comprising inserting a scaffold into a bone defect; transducing one or more cells with a growth factor essential for bone formation; and loading the one or more cells into the scaffold.

In embodiments, the bone defect is a critically sized defect such that it is incapable of healing on its own.

In embodiments, the one or more cells are stem cells. In embodiments, the stem cells are adipose derived stem cells. In embodiments, the one or more cells are bone marrow cells. In embodiments, the bone marrow cells are rat bone marrow cells.

In embodiments, the growth factor essential for bone formation is bone morphogenetic protein 2.

In embodiments, transducing the one or more cells with a growth factor essential for bone formation comprises transducing the cells with one or more vectors. In embodiments, transducing the cells with one or more vectors comprises transducing the cells with a lentiviral vector system. In embodiments, the lentiviral vector system comprises a trans-activator vector and a vector encoding the growth factor essential for bone formation. In embodiments, the growth factor essential for bone formation is bone morphogenetic protein 2.

In embodiments, the scaffold is comprised of calcium phosphate. In embodiments, the scaffold is comprised of tri-calcium phosphate.

In an aspect a method for repairing a bone defect of a patient is provided, comprising providing a 3D model of a scaffold for bridging the bone defect, providing a ceramic scaffold comprising calcium and phosphate based on the 3D model, and loading the ceramic scaffold with cells transduced with a growth factor essential for bone formation.

In embodiments, the method further comprises forming the ceramic scaffold by 3D printing a calcium phosphate material. In embodiments, providing the 3D model comprises shaping the 3D model for causing the ceramic scaffold to match undamaged areas adjacent to the bone defect, so as to fit against the undamaged areas while spanning the bone defect. In embodiments, providing the ceramic scaffold comprises forming a plurality of holes in the range of 300µ to 1000µ in the ceramic scaffold.

In embodiments, the method further comprises preparing the cells transduced with the growth factor by transducing the cells with a lentiviral vector system comprising (i) a trans-activator vector and (ii) a vector encoding the growth factor essential for bone formation. In embodiments, the growth factor essential for bone formation is bone morphogenetic protein 2.

To the accomplishment of the foregoing and related ends, one or more examples comprise the features hereinafter particularly pointed out in the claims and fully described in the detailed description after the drawings.

BRIEF DESCRIPTION OF THE DRAWINGS

FIG. 11A shows a femoral radiograph 12 weeks after treatment demonstrating complete bridging of defect site (see, arrows). FIG. 11B shows coronal micro-computed tomography image of a femur 12 weeks after treatment. Robust healing across the defect site is seen with reconstitution of the bony cortex.

DETAILED DESCRIPTION

The present disclosure concerns use of regional gene therapy with growth factor transduced cells in bone graft scenarios with 3D-printed scaffolds. The combination of these technologies represents an innovative method of grafting bone with many potential clinical applications.

Definitions

As used herein, the phrase "a critically sized defect" or "a critically sized bone defect" refers to a bone defect that is in capable of healing on its own. As used herein, the phrase "a critically sized femoral defect" refers to a femoral defect that is incapable of healing on its own. As used herein, the phrase "a critically sized rat femoral defect," or "a rat critically sized femoral defect" refers to a rat femoral defect that is incapable of healing on its own.

As used herein, the initials "ADSC" refer to adipose-derived stems cells.

As used herein, the initials "BMP-2" refer to the bone morphogenetic protein 2.

As used herein, the initials "CaP" refer to calcium phosphate.

As used herein, the initials "G5" refer to a Gal4 responsive promoter.

As used herein, the initials "LV" refer to a lentiviral vector.

As used herein, the initials "RhMLV" refer to a murine leukemia virus long terminal repeat promoter.

As used herein, the initials "TCP" refer tri-calcium phosphate.

As used herein, the phrase "trans-activator vector" is any vector capable of mediating induction of a target gene. In embodiments, a "trans-activator vector" encodes a transcription factor. In embodiments, the transcription factor is Gal4.

As used herein, the phrase "two-step transcriptional amplification (TSTA) system" refers to any gene expression system in which transcription of a target gene is preceded by expression of a gene that drives expression of the target gene. In embodiments, the TSTA system is a vector system. In embodiments, the vector system is a lentiviral vector system.

DESCRIPTION OF THE EMBODIMENTS

Figure 5:
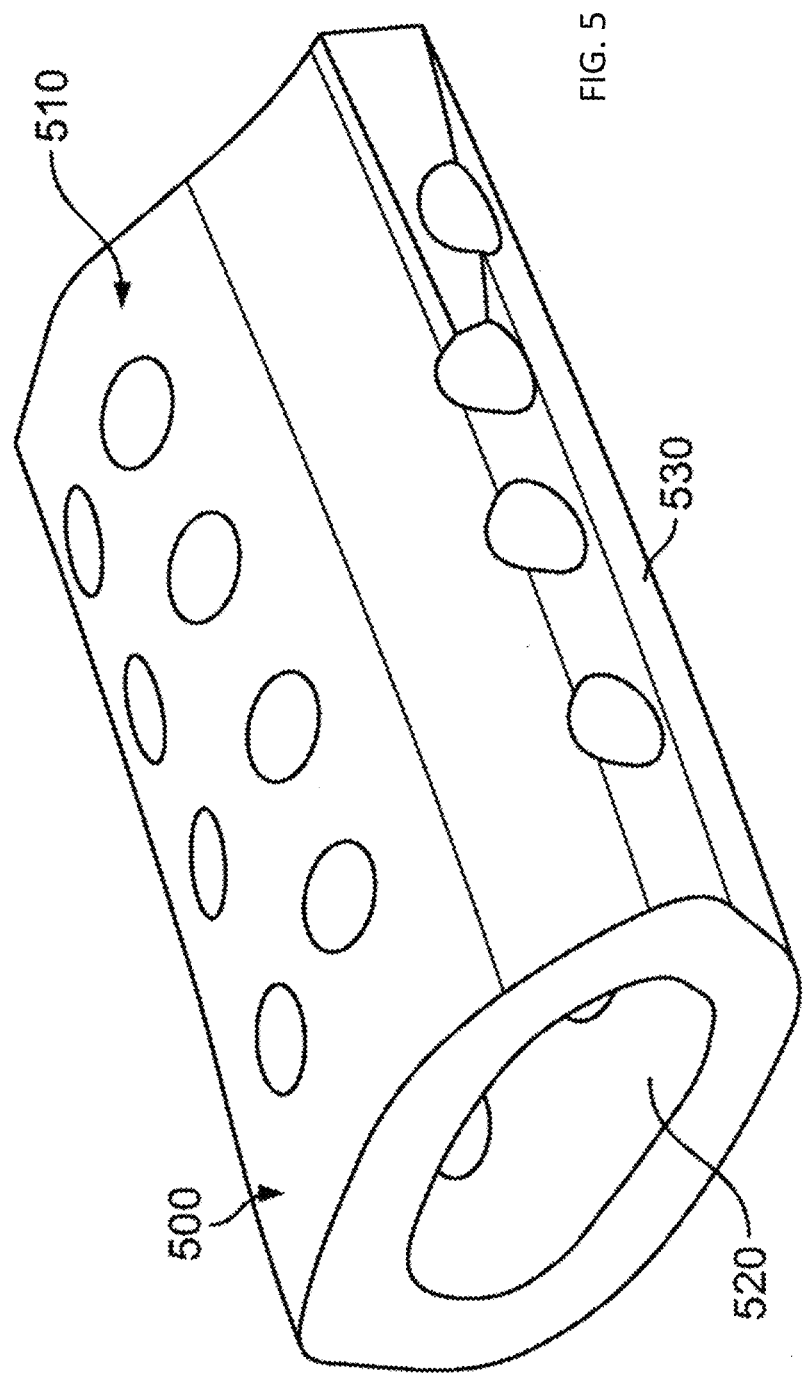
FIG. 5 is a perspective view showing an example of a 3D printed ceramic scaffold for bone repair.

In an aspect, and with reference to FIG. 5, prior to surgical implantation, the scaffold and loaded cells form an assembly made of a ceramic scaffold 500 configured for spanning the bone defect, and a culture of live mesenchymal stem cells 200 or other growth factor transduced cells incorporating a gene that encodes a growth factor essential for bone formation loaded onto the ceramic scaffold. Suitable cells for being transduced with one or more genes that encode a growth factor may include, for example, mesenchymal cells, bone marrow cells, fibroblasts, adipose-derived cells, umbilical cord cells, or muscle cells. The ceramic material may include, for example, CaP or beta TCP. In a clinical setting, the assembly may be prepared in advance of surgery and maintained alive in vitro until surgical implantation. In an alternative, the surgeon may load live growth factor transduced cells on the ceramic scaffold for the first time after it is in place in the patient's body (in vivo), or may supplement an in vitro loading of cells with a second application in vivo.

In embodiments, and with reference to FIG. 5, the scaffold may be thinner than the bone wall to be repaired and perforated with circular openings 510 in the range of about 300 to 1000 microns, for example, about 500 to 700 microns, or about 700 microns. In embodiments, the openings 510 may be spaced as desired to facilitate bone regrowth, for example, uniformly or semi-uniformly center-to-center spaced at about 1.5 to 5 times the opening's largest diameter. In embodiments, the scaffold is generally tube-shaped with an interior surface 520 and exterior surface 530. In embodiments, the assembly of scaffold and live growth factor transduced cells enables regeneration of structural bone tissue from the loaded cell culture on its openings 510, exterior 530, interior 520 and by recruitment of local progenitor cells.

In an aspect, a method of repairing a bone defect is provided comprising transducing one or more cells with a growth factor and loading the cells into a scaffold that has been implanted into a bone defect.

In embodiments, the bone defect is a critically sized defect such that the bone defect is incapable of healing on its own.

In embodiments, the cells transduced with a growth factor are stem cells. In embodiments, the stem cells are adipose derived stem cells (ADSCs). In embodiments, the stem cells can be derived from any suitable source of stem cells. In embodiments, the cells transduced with a growth factor are bone marrow cells. In embodiments, the bone marrow cells are rat bone marrow cells. In embodiments, the bone marrow cells can be derived from any suitable bone marrow source.

In embodiments, the growth factor is any factor that stimulates growth of any type of tissue. In embodiments, the growth factor stimulates growth of epithelial tissue. In embodiments, the growth factor stimulates the growth of bone. In embodiments, the growth factor is BMP-2.

In embodiments, the cells are transduced with one or more vectors. In embodiments the one or more vectors comprise a vector system. In embodiments, the vector system is a lentiviral vector system. In embodiments, the lentiviral vector system is a two-step transcriptional amplification (TSTA) system. In embodiments, the TSTA system comprises two different vectors: a first vector and a second vector. In embodiments, the first vector is a trans-activator vector. In embodiments, the trans-activator vector is the vector LV-RhMLV-Gal4. In embodiments, the second vector is a vector that encodes BMP-2. In embodiments, the vector that encodes BMP-2 is the vector LV-G5-BMP-2.

In embodiments, the scaffold is a ceramic scaffold. In embodiments, the ceramic scaffold is made up of a material comprised of calcium phosphate (CaP). In embodiments, the ceramic scaffold is made up of a material comprised of tri-calcium phosphate (TCP). In embodiments, the scaffold is made up of any other suitable material.

Flowcharts and Methods

Figure 4:
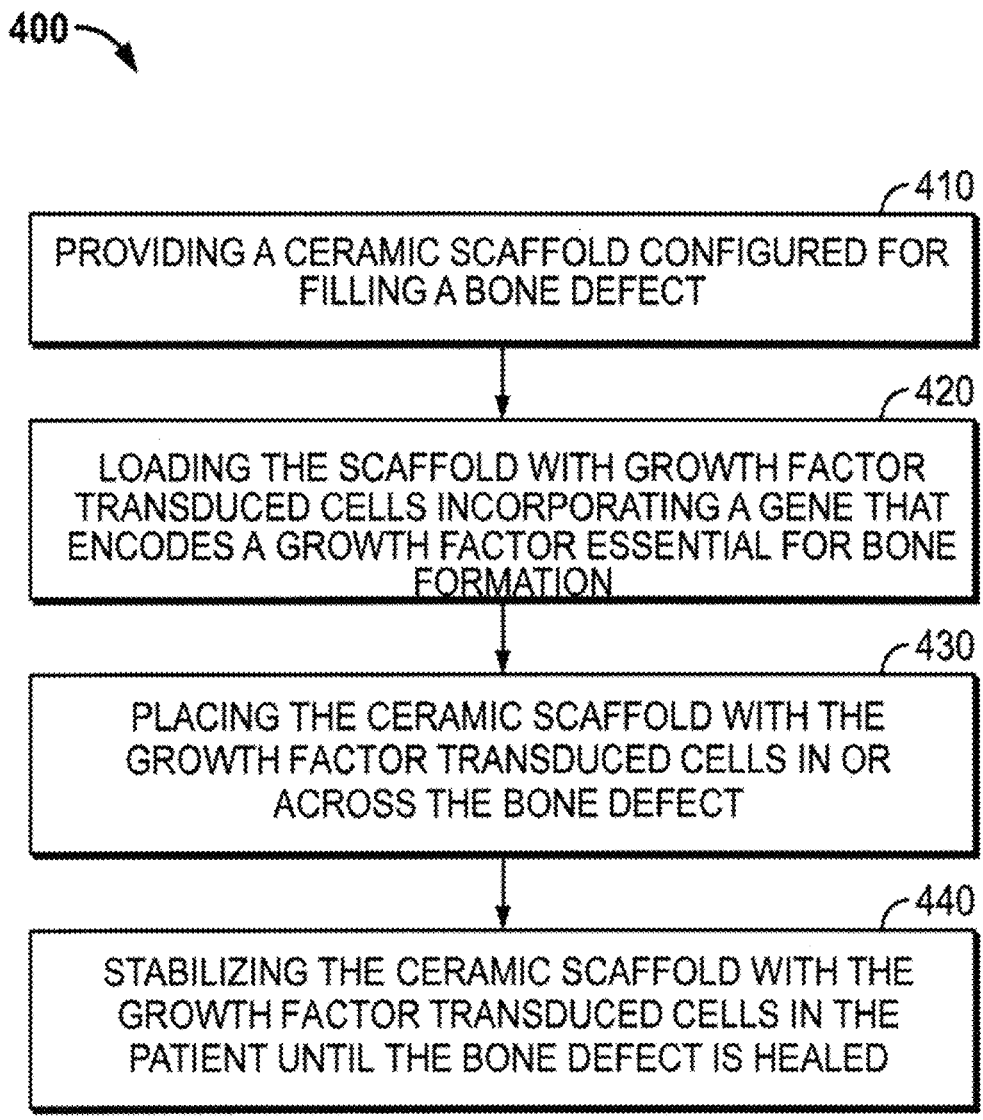
FIG. 4 is a flowchart illustrating operations and aspects of a method for repair of a bone defect.

Referring to FIG. 4, an exemplary method 400 for repairing a bone defect of a patient may include, at 410, providing a ceramic scaffold configured for spanning the bone defect, for example, by 3D printing a CaP or other ceramic scaffold or by obtaining a pre-printed scaffold from a manufacturer sized to span the bone defect, for example based on a preceding CT scan as for the rodent femur described above. The method 400 may further include, at 420, loading the scaffold with growth factor transduced cells incorporating a gene that encodes a growth factor essential for bone formation, for example, by preparing or obtaining a culture of lentiviral transduced bone marrow cells as described herein, applying the culture to the scaffold, and confirming viability of the culture loaded on the scaffold prior to implantation. For example, the scaffold with pre-loaded mesenchymal cells as described may be obtained in the form of a prepared assembly from an independent source, e.g., a specialized laboratory, or the cell preparation and loading of the scaffold may be performed by a laboratory controlled by the facility performing the scaffold-implantation Surgery. The method may further include, at 430, placing the ceramic scaffold with the growth factor transduced cells in or across the bone defect.

The method 400 may further include, at 440, stabilizing the ceramic scaffold with the growth factor transduced cells in the patient until the bone defect is healed, using any suitable stabilizing technique. The ceramic scaffold is semi-structural and designed for load sharing. The scaffold may not be strong enough by itself to stabilize the defect without load sharing from other structural members. Depending on the nature of the defect, it may be stabilized using bio-compatible metal plates, rods, or other suitable structural members.

The enumerated operations 410, 420, 430, 440 may be performed in any operable order with suitable modifications. For example, the operation 430 placing the ceramic scaffold in or across the defect may be performed, but without first loading growth factor transduced cells onto the ceramic. Then, the operation 420 of loading the scaffold with growth factor transduced cells may be performed while the scaffold is in place around the defect. For example, the growth factor transduced cells may be suspended in a bio-compatible fluid and applied to the ceramic scaffold in vivo or in vitro, using a pipette or other suitable fluid applicator.

Figure 6:
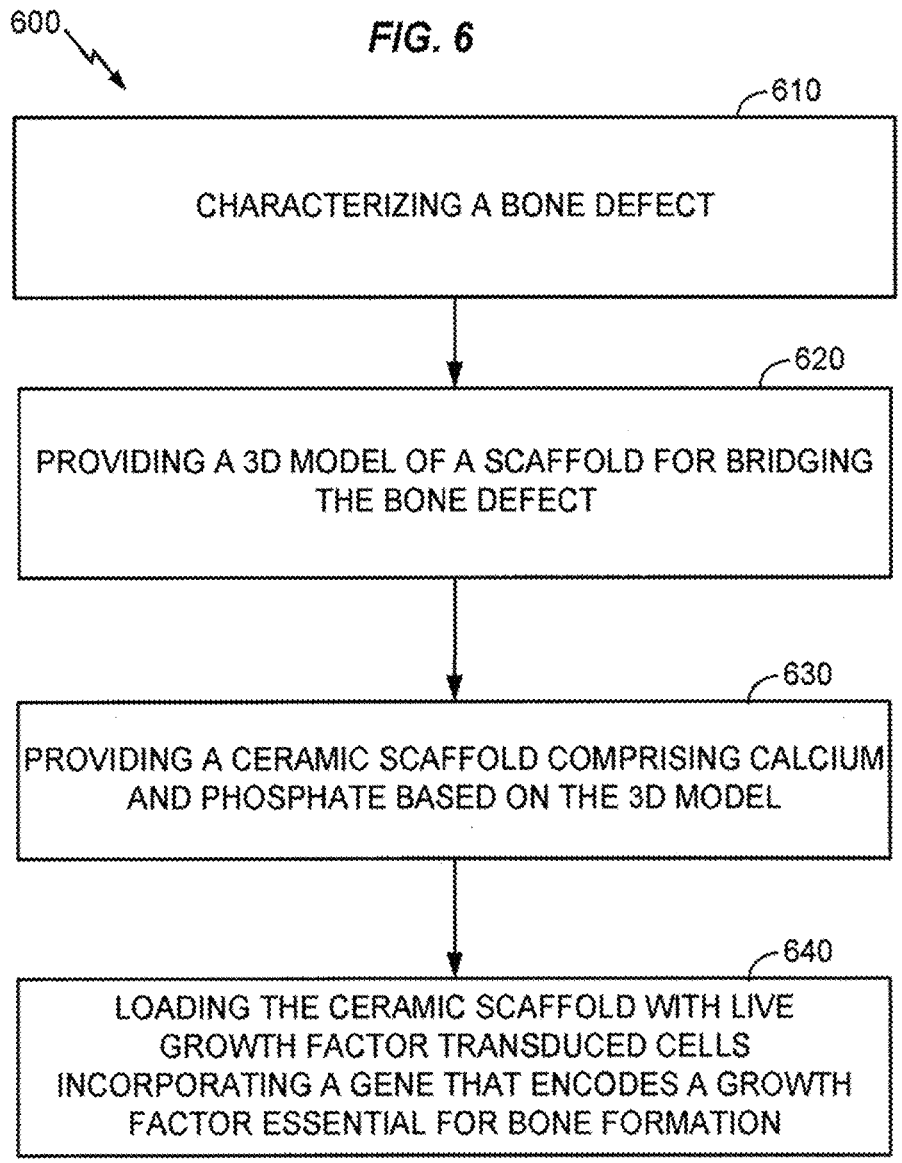
FIG. 6 is a flow chart illustrating operations and aspects of making a ceramic scaffold with the growth factor transduced cells.

Referring to FIGS. 4, 5, and 6, further aspects of the present disclosure may include a method 600 for making a ceramic scaffold 500 loaded with growth factor transduced cells as described herein, for use in the method 400 or other suitable method. The method 600 may include, at 610, characterizing a specific bone defect of a patient. For example, the operation 610 may include scanning a bone defect by a 3D scanner, for example, a CT scanner, digitizing 30 information obtained by the scanning, and associating the digitized information with an identifier for the patient and defect site. In an alternative, the characterizing 610 may include receiving information that associates an identifier for a patient and/or bone defect with 3D information relating to the defect or to a scaffold for bridging the defect.

Referring to FIG. 6, further aspects of the method 600 may include, at 620, providing a 3D model of a scaffold for bridging the bone defect characterized by the first operation 610. As used herein, "providing" includes but is not limited to engaging a person or entity to create the 3D model based on the data characterizing the bone defect. For example, a medical technician may design a 3D model to fit stable portions of the bone that are expected to remain as scanned after the bone defect is prepared for repair, e.g., by cleaning out damaged tissue. The stable regions of the bone may be adjacent to defective regions of the bone.

The method 600 may further include, at 630, providing a ceramic scaffold that includes calcium and phosphate or that consists essentially of calcium and phosphate materials, based on the 3D model provided by the preceding operation 620. Providing may include manufacturing the ceramic scaffold, or obtaining the ceramic scaffold from a manufacturer or supplier. A slurry-based stereolithography 3D printing method as described by Dr. Song Chen (see reference herein above) may be used to manufacture the ceramic scaffold. The manufacturing may include mixing a powdered calcium-phosphate ceramic or pre-ceramic material with a photopolymer resin to create a slurry as feedstock for a stereolithographic additive manufacturing process (e.g., using tape casting as described above), thereby forming a "green" pre-fired scaffold. The green scaffold, which may include a mixture of ceramic and organic resin and/or a pre-ceramic polymer, may be heated under suitable conditions (e.g., oxidizing or non-oxidizing, depending on the process used) to purge non-ceramic materials and/or transform a pre-ceramic material into a ceramic material. At 630, the method comprises forming the ceramic scaffold 500 made of a calcium phosphate material, alone or in combination with other materials. Likewise, the method may include manufacturing the scaffold using a 3D printing technique as described herein above, or other suitable method. 3D printing may be especially advantageous for forming the ceramic-resin scaffold when it is desired to custom shape the ceramic-resin scaffold to match an individual morphology of the bone in healthy areas surrounding the defect.

For example, referring to FIG. 5, the ceramic-resin scaffold may be formed to have an inner surface 520 matching an outer surface of the healthy bone areas. Forming the ceramic-resin scaffold 500 may also include forming a plurality of holes 510 having diameters in the range of about 300μ to 1000μ (e.g., in the range of 500μ to 700μ, or about 7000μ) in the ceramic-resin scaffold, for example during the 3D printing process.

Referring to FIG. 6, the method 600 may further include, at 640, loading the ceramic scaffold with live growth factor transduced cells incorporating a gene that encodes a growth factor essential for bone formation. As discussed above, loading may be performed in vitro, in vivo, or both. In other embodiments, the growth factor transduced cells may be prepared for incorporating the gene that encodes the growth factor by transducing the gene into the growth factor transduced cells. For example, the method may include preparing the growth factor transduced cells incorporating the gene that encodes the growth factor by a lentiviral based transcriptional activation system expressing bone morphogenetic protein 2.

Having thus described embodiments of methods and apparatus for repairing a bone defect or providing a ceramic scaffold loaded with growth factor transduced cells, it should also be appreciated that various modifications, adaptations, and alternative embodiments thereof may be made within the scope and spirit of the present invention. For example, 3D printed calcium ceramic scaffolds have been disclosed, but the inventive concepts described above may be equally applicable to scaffolds of other ceramic materials, or scaffolds made by other manufacturing methods than disclosed herein above. In addition, a culture of growth factor transduced cells incorporating a gene that encodes a growth factor essential for bone formation may be prepared by any suitable method whether or not described herein.

EXAMPLES

Example 1

3D Printing

Calcium phosphate (CaP) scaffolds were 3D printed using a slurry-based stereolithography process as developed by Dr. Song Chen et al. in Ceramic Fabrication Using Mask-Image-Projection-based Stereolithography: Integrated with Tape-casting. *Journal of Manufacturing Processes,* 2015; 20(3): 456-464. Briefly, this 3D printing technique is performed by first mixing a ceramic powder with a photopolymer resin to create a slurry. A tape casting system is used to aid the recoating of each slurry layer. A light source then activates the resin, curing it layer by layer until an object is built. The object, which is still a mixture of ceramic and resin, is then heated in a furnace to burn out the resin. Since the resin has a much lower melting temperature than the ceramic, the ceramic part of interest is left behind as the final product.

Computer Aided Software (CAD} was first used to create a hollow elliptical cylinder 6 mm in length in order to approximate the size and shape of a rat critically sized femoral defect. These scaffolds were 3D printed using commercially available calcium phosphate powder (Alfa Aesar #89836). An example of a resulting scaffold 500 is shown in FIG. 5.

Example 2

Regional Gene Therapy

Virk et al. 2011 ("Same day" ex-vivo regional gene therapy: a novel strategy to enhance for bone repair. *Mo/Ther.* 2011; 19:960-968) describes the gene therapy in detail. Briefly, a lentiviral based system (LV-BMP2) was created expressing bone morphogenetic protein 2 (BMP-2). Cultured rat bone marrow cells were transduced using a multiplicity of infection (MOI) of 25. These cells were used in the experiments detailed below.

Example 3

In Vitro BMP-2 Production

BMP-2 production of transduced RBMC was tested in vitro after 48 hours and 14 days of cell culture on 15 mm diameter, 2 mm thick 3D printed discs. At 48 hours BMP-2 production was higher on 3D-printed scaffolds as compared to control (Table 1).

TABLE 1

Comparison of BMP-2 production in 3D-printed scaffolds compared to control

|  | 48 Hours | 14 Days |
|---|---|---|
| Non-transduced PBMC | 0.00 | 0.03 |
| LV-BMP2 + 3D disc | 1.71 | 48.62 |
| LV-BMP2 | 1.26 | 157.32 |

Based on our work, in vitro BMP-2 production on the 3D printed discs is sufficient to heal a critically sized rat femoral defect.

Example 4

In Vitro Cell Viability

Figure 1:
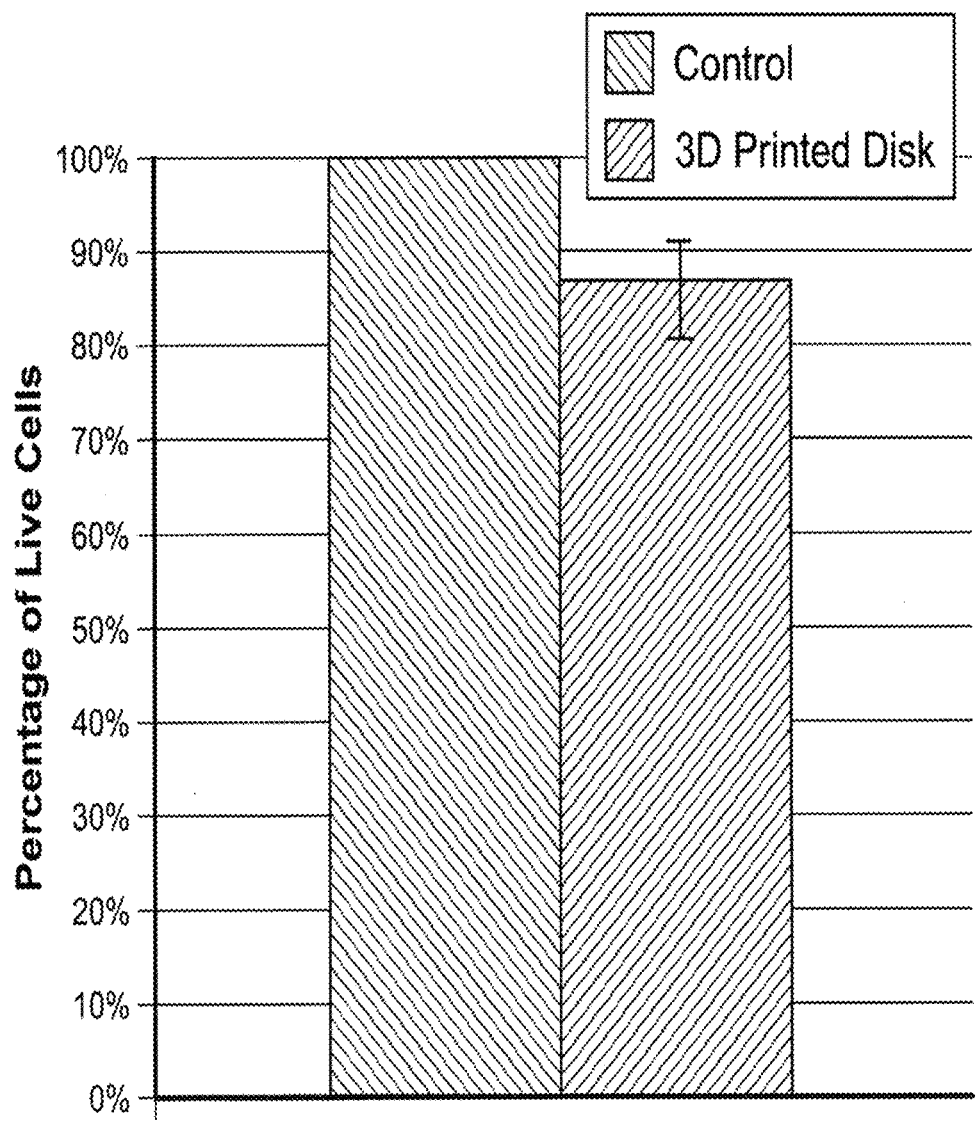
FIG. 1 is a chart showing in vitro results of a trial using gene therapy in conjunction with a 3D printed ceramic scaffold.
Figure 2:
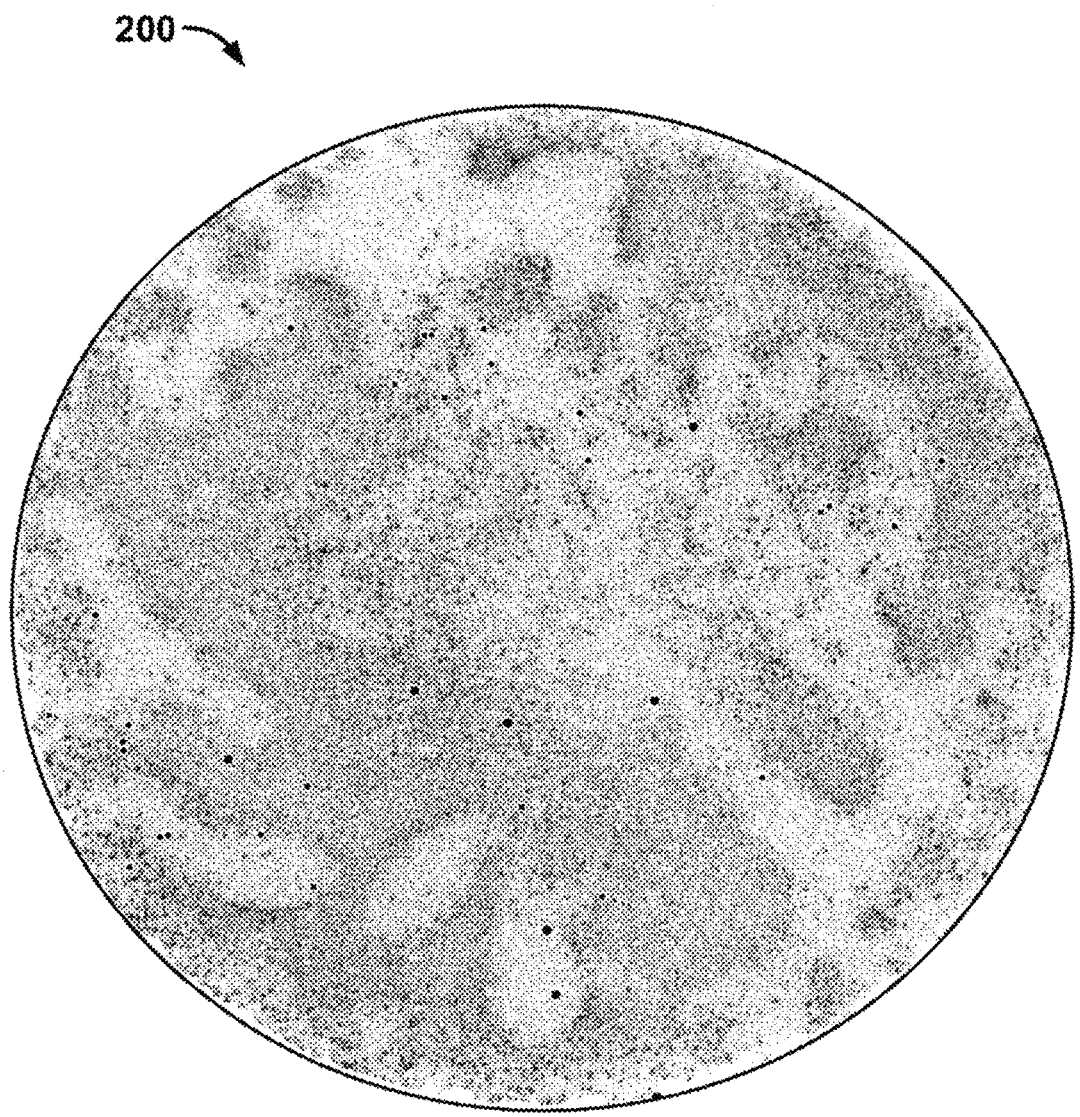
FIG. 2 is a grayscale rendering of a photo illustrating cell viability of transduced cells on a 3D printed ceramic scaffold disk after 72 hours.

Transduced rat bone marrow cells (RBMC) were cultured in vitro on top of 3D printed CaP discs for 72 hours. Cell viability was determined using a commercially available Live/Dead assay kit (BioVision K501). Cells cultured on CaP disks demonstrated excellent viability at 72 hours compared to a control (standard culture well). Cell viability on 3D printed discs averaged 85% (SD 6%) relative to the control (FIG. 1 and FIG. 2, 200). These cell viability results are higher than a published study using comparable 3D printed calcium phosphate/collagen combination scaffolds (Inzana J, Olvera D, Fuller S, et al. 3D printing of composite calcium phosphate and collagen scaffolds for bone regeneration, *Biomaterials.* 2014; 35:4026-4034).

Example 5

In Vivo Bone Formation

Figure 3:
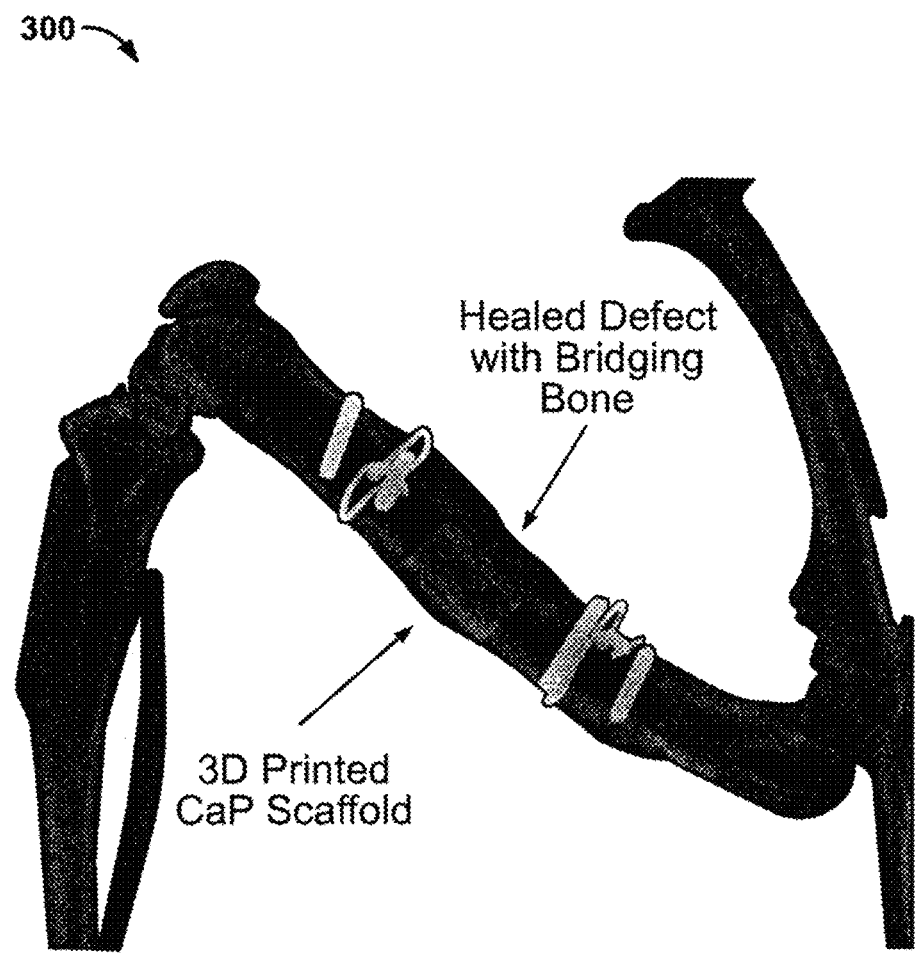
FIG. 3 is an X-ray image showing results of a successful rat bone repair using a method as disclosed herein.

A pilot experiment using a 12-week-old Lewis rat was performed. A standard 6-mm mid diaphyseal femoral defect was created as described in prior publications (Alae, F., Liebermen, J. R., et al., *Biodistribution of LV-TSTA transduced rat bone marrow cells used for "ex-vivo" regional gene therapy for bone repair Curr Gene Ther.* 2015; 15(5): 481-491, and Virk et al. *"Same-day" ex-vivo regional gene therapy: A novel strategy to enhance bone repair,* (2011) Molecular Therapy 19(5), 960-968). A 3D printed CaP scaffold loaded with 5 million lentiviral transduced rat bone marrow cells was placed in the defect. The defect was healed 8 weeks after the surgical procedure (FIG. 3 at x-ray image 300). The 3D printed CaP scaffold itself and the regenerated "bridging bone" are clearly visible and pointed out in FIG. 3. A drawing of a model for a similar 3D printed CaP scaffold 500 is shown in FIG. 5. FIG. 2 shows a culture 200 of mesenchymal stem cells incorporating a gene that encodes a growth factor essential for bone formation, grown on a CaP ceramic disk.

Example 6

Scaffold Shaping and Configuration

More recently, Computed Tomography (CT) data from an intact rodent femur was obtained from previous work. Commercially available software (Mimics; Materialise N V, Leuven, Belgium) was then used to convert a 6 mm section of diaphyseal bone into a file type compatible with 3D printing software, resulting in a model of a scaffold 500 as shown in FIG. 5. Additionally, 700-micrometer holes 510 were added to the model scaffold to facilitate cellular growth and communication.

An alternative ceramic powder, beta tri-calcium phosphate (beta TCP), may also be used to 3D print the scaffolds. We have 3D printed scaffolds based on the "rodent specific" CT data. These may be tested following similar methods as described above.

Example 7

Using 3D Printed Scaffolds to Heal Critically Sized Bone Defects in a Rat Model

Materials and Methods

3D Printed Scaffold: Computed tomography (CT) scans of the intact femur of a 24-week-old male Lewis rat were taken as DICOM image files and converted into a 3D stereolithography (STL) file using commercial software (Mimics; Materialise N V, Leuven, Belgium). A 6 mm section of the mid diaphysis was taken from the model and multiple 700 µm holes were added to facilitate cellular communication and vascular ingrowth throughout the scaffold (FIG. 1*b*) (Karageorgiou & Kaplan, *Porosity of 3D biomaterial scaffolds and osteogenesis, Biomaterials,* 26(27), 5474-5491 (2005)). The 700 µm pores were the only source of porosity in the scaffold. A projection-based ceramic STL process was used to fabricate Tricalcium phosphate (TCP) scaffold structures to precisely fit a 6 mm rat femoral defect based on the DICOM image. This process creates a complex TCP structure via solidifying a viscous slurry-mixture of photocurable resin (Formlabs, Somerville, MA) and TCP powder (Ceramisys; Sintered beta-Tricalcium Phosphate, Sheffield, United Kingdom) with a customized ultraviolet (UV) light engine in a layer-by-layer fashion, followed by high-temperature post-processing for removing the resin and densifying the TCP particles (Song, Chen, Lee, Wu, & Cheng, *Ceramic fabrication using mask-image-projection-based stereolithography integrated with tape-casting, Journal of Manufacturing Processes,* 20(3) 456-465 (2015)).

X-ray Diffraction Analysis: X-ray diffraction (XRD) (Ultima IV Diffractometer, Rigaku, Tokyo, Japan) analysis was performed to characterize the molecular compounds contained within the synthesized scaffold based on diffraction patterns. The 3D printed TCP scaffold was crushed into its powder form prior to XRD characterization. XRD was performed from 15° to 75° at a speed of 6° per minute (dpm). A zero-diffraction slide was used to minimize background noise. Diffraction pattern analysis was completed using Jade 9 software (KS Analytical Systems, Aubrey, TX). A pure powder TCP sample from which the 3D printed TCP scaffold was synthesized served as a control. Figure of merit (FoM) was calculated for the crushed scaffold and the pure powder TCP sample to allow for comparisons of the composition.

Figure 7A:
FIG. 7A depicts a stereolithography (STL file created from a computed tomography (CT)) scan of a rodent femur.

Rat Bone Marrow Cell Isolation and Transduction: Rat bone marrow cells (RBMCs) were harvested from tibias and femurs of 8-week-old rats (Male Lewis Rats; Charles River Laboratories, Wilmington, MA) (Sugiyama et al., *Lentivirus-mediated gene transfer induces long-term transgene expression of BMP-2 in vitro and new bone formation in vivo,* Molecular Therapy, 11(3), 390-398 (2005)) (FIG. 7A depicts a computed tomography scan of a rodent femur). The resulting cell pellet was resuspended in Iscove's modified Dulbecco's media (IMDM) (ThermoFisher Scientific, Waltham, MA) and supplemented with 15% fetal bovine serum (FBS) (Omega Scientific, Tarzana, CA), streptomycin 100 µg/mL and penicillin 100 U/mL, and plated on a 100 mm dish for culture-expansion. When 90-100% confluent, adherent cells were trypsinized and passaged with plating 0.7-1×10 (Carragee et al., *A critical review of recombinant human bone morphogenetic protein-2 trials in spinal surgery: Emerging safety concerns and lessons learned,* The Spine Journal, 11(6), 471-491 (2011)) cells per dish. Passage 3 cells were transduced with a lentiviral vector carrying the cDNA for BMP-2 (LV-BMP-2) or green fluorescent protein (GFP) (LV-GFP) at a multiplicity of infection of 25 in the presence of 8 µg/mL polybrene (Sigma, St. Louis, MO).

Study Groups: There were four groups in the study, one experimental group (group 1) and three negative control groups (groups 2-4) (Table 2). Rats were randomly assigned to each group.

Figure 7B:
FIG. 7B depicts a tricalcium phosphate (TCP) scaffold with 700 μm pores from a 3D printed to fit a critically sized rat femoral defect.
Figure 7C:
FIG. 7C depicts an intraoperative photograph demonstrating placement of the 3D printed TCP scaffold (middle arrow) with the rat femoral defect (the left arrow points to the distal femoral segment and the right arrow points to the proximal femoral segment).

Rat Femoral Defect Model: The study was conducted in compliance with Institutional Animal Care and Use Committee (IACUC) regulations. A 23 mm×4 mm×4 mm polyethylene four-hole plate was secured to the left femur both proximally and distally with threaded wires and cerclage wires in a 12-week-old male Lewis rat. A standard 6 mm femoral defect was created with a high-speed burr (Lieberman et al., 1999). This is a critically sized defect and will not heal without a robust osteo-inductive stimulus. The periosteum was removed, and the intramedullary canals were flushed with normal saline solution to remove remaining osteoprogenitor cells from the defect site. The 3D printed TCP scaffold specifically designed to fit the femoral defect was injected with 5 million RBMCs diluted in phosphate-buffered saline (PBS) from groups 1-3 just before implantation or left empty for animals in group 4. FIG. 7B depicts an exemplary embodiment of a tricalcium phosphate scaffold with 700 μm pores. The scaffold was then inserted into the bone defect (FIG. 7C) and secured with two circumferential Vicryl sutures. Overlying muscle was closed with Vicryl suture further securing the scaffold in place. Animals were allowed to weight-bear immediately after surgery.

Radiographic Analysis: Plain radiographs of all operated femurs were taken at 4, 8, and 12 weeks after the surgical procedure using a Faxitron imaging system (Faxitron Bioptics, Tucson, AZ). The radiographs were assessed to determine whether the defect had healed. Three blinded observers graded healing of the defect from 0 to 5 where 0 represents no healing and 5 represents complete healing defined as bridging of both cortices. Radiographs taken at 8 and 12 weeks were graded.

Microcomputed Tomography: A microcomputed tomography (micro-CT) scan (μCT40, Scanco Medical, Bassersdorf, Switzerland) was performed on all of the operated femurs after euthanasia at 12 weeks to assess bone volume formed at the femoral defect (Virk et al., "Same-day" ex-vivo regional gene therapy: A novel strategy to enhance bone repair, Molecular Therapy 19(5), 960-968 (2011)). The amount of cortical bone and trabecular bone formed (bone volume) within the femoral defect region (tissue volume) was calculated after the TCP scaffold was digitally subtracted. The total volume of bone formation (bone volume fraction (BVF)=bone volume (BV)/tissue volume (TV)) was calculated and average BVF ratios were compared for each group.

Histologic and Histomorphometry: A total of 19 femurs were analyzed histologically (Table 2). Five millimeter axial and transverse sections were cut, allowing for analysis in two planes with hematoxylin & eosin (H&E), Masson's trichrome, and tartrate-resistant acidic phosphatase (TRAP) staining. Each specimen was evaluated for the presence of cortical bridging across the femoral defect site, inflammation, and presence of osteoclasts. Following staining, axial images were analyzed with Bioquant analysis software (Bioquant Image Analysis, Nashville, TN) under 1× magnification. Bone area (BA) and tissue area (TA) were selected using the Bioquant software. The two axial histologic images were analyzed, and the mean BA/TA ratio was averaged for each femur. Mean BA/TA ratios were calculated for each study group and compared.

TABLE 2

Study groups and studies of the defects

| Treatment Group | # of total defects | # that were studied radiographically | # that were studied with micro-CT | # that were studied histologically and histomorphometrically | # that were studied biomechanically |
|---|---|---|---|---|---|
| Group 1: LV-BMP2 + TCP scaffold | 14 | 14 | 14 | 5 | 9 |
| Group 2: LV-GFP + TCP scaffold | 5 | 5 | 5 | 5 | 0 |
| Group 3: Non-transduced RBMCs + TCP scaffold | 5 | 5 | $4^a$ | $4^a$ | 0 |
| Group 4: TCP scaffold without cells | 5 | 5 | 5 | 5 | 0 |

$^a$One rat failed fixation at the 8-week time point and was euthanized prior to the 12-week time point and therefore did not undergo micro-CT or histology staining.

TABLE 3

Radiographic outcomes

| Treatment Group | 4 weeks Score | 4 weeks # with complete healing | 8 weeks Score | 8 weeks # with complete healing | 12 weeks Score | 12 weeks # with complete healing |
|---|---|---|---|---|---|---|
| Group 1: LV-BMP2 + TCP scaffold | N/A | 2 (14%) | 4.78 +/− 0.30 | 8 (57%) | 4.93 +/− 0.14 | 13 (100%) |
| Group 2: LV-GFP + TCP scaffold | N/A | 0 (0%) | 0.3 +/− 0.32 | 0 (0%) | 0.67 +/− 0.71 | 0 (0%) |
| Group 3: Non-transduced RBMCs + TCP scaffold | N/A | 0 (0%) | 0.2 +/− 0.32 | 0 (0%) | 0.33 +/− 0.19 | 0 (0%) |

TABLE 3-continued

Radiographic outcomes

| Treatment Group | 4 weeks | | 8 weeks | | 12 weeks | |
|---|---|---|---|---|---|---|
| | Score | # with complete healing | Score | # with complete healing | Score | # with complete healing |
| Group 4: TCP scaffold without cells | N/A | 0 (0%) | 0.9 +/− 0.59 | 0 (0%) | 1.07 +/− 1.01 | 0 (0%) |

Biomechanical Testing: The operative femur from nine specimens in the experimental group (group 1) underwent biomechanical testing. The contralateral, unoperated femur of each animal was also tested to serve as a control. The surrounding soft tissue, pins, wires, and plate were removed from each specimen prior to testing. Each specimen was frozen and then thawed right before testing. All testing was conducted on the same day to minimize variation due to temperature or biomechanical setup.

Each end of the specimen was potted in polymethylmethacrylate blocks and mounted on a torsional testing fixture such that the longitudinal bone axis was centered with the axis of torsion. The torsional testing fixture and specimen were attached to a universal testing machine (Minneapolis, MN). Using a rate of 15 per minute, the distal end of the specimen was internally rotated until bone failure. Torsional stiffness, maximum torque, peak displacement, and total energy for failure were calculated and the mean values for the operative and intact contralateral femurs were compared.

Statistical Analysis: Statistical analysis was performed using IBM SPSS Statistics 21. The results are given as mean and SD. The data were first checked for normality using Shapiro-Wilk test. One-way ANOVA and post-hoc analysis with Tukey's range test were done for comparisons in X-ray scores as well as BV and BVF between the different treatment groups. Biomechanical parameters between the operated and intact contralateral limbs were compared using Mann-Whitney U test.

Results

Scaffold Composition: The XRD pattern for the pure TCP powder was most similar to calcium phosphate with a FoM of 6.8 and 92% composition similarity. The XRD pattern for the 3D printed TCP scaffold was also most similar to calcium phosphate with a FoM of 7.5 and 92% composition similarity.

Figure 8:
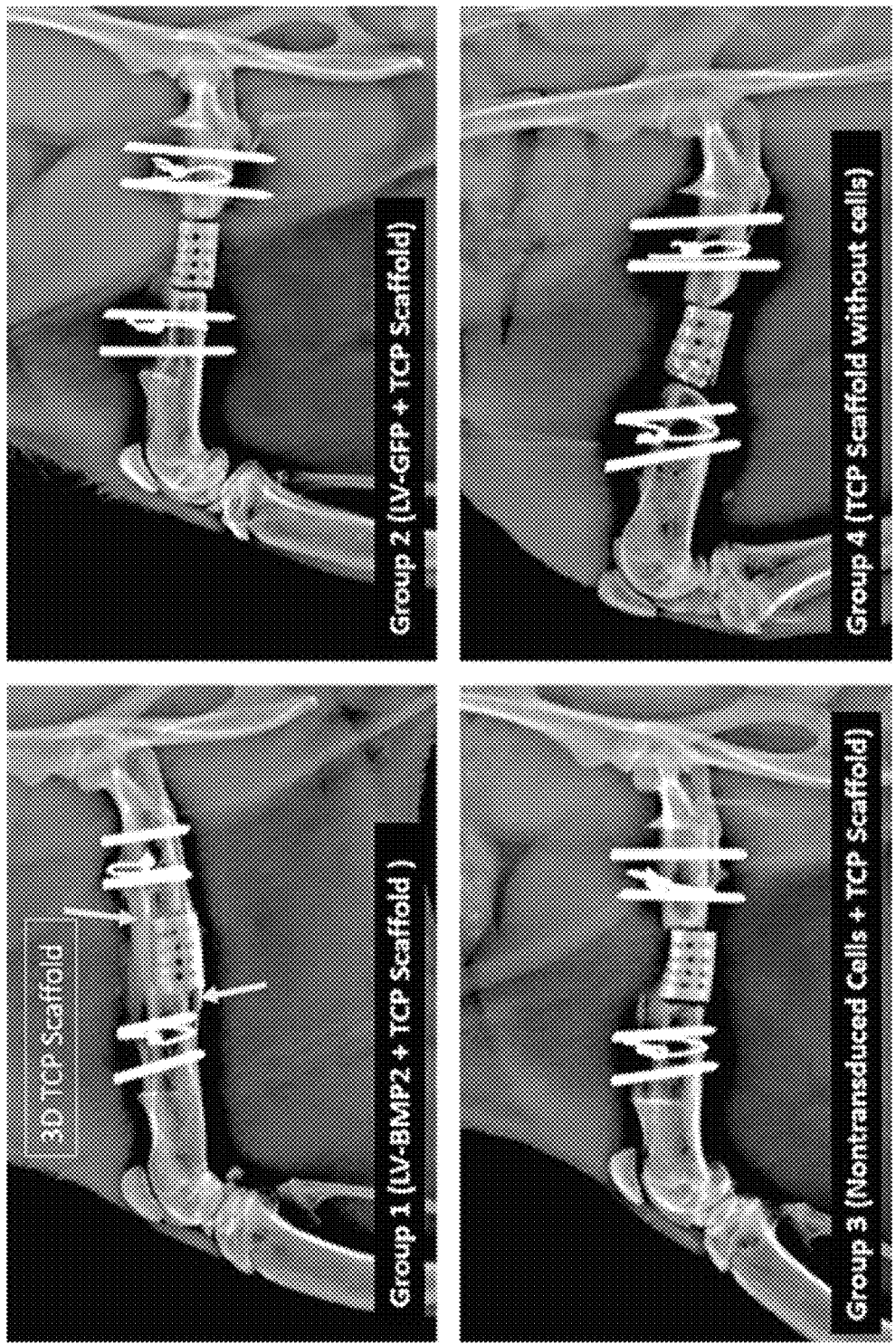
FIG. 8 depicts representative plain radiographic images from groups 1-4 taken at 12 weeks after insertion of the 3D printed TCP scaffold. Group 1 demonstrated complete healing of the defect. The arrows illustrate bone surrounding the scaffold, bridging the defect proximally and distally.

Radiographic Outcomes: All femurs (14 out of 14) in group 1 demonstrated complete healing of the bone defect at the 12-week time point with an average score of 4.93±0.14 (Table 3 and FIG. 8). Plain radiographs demonstrated robust bone formation around the 3D printed TCP scaffold and across the defect at 12 weeks. Prior to the 12-week time point, two femurs (14%) had healed at 4 weeks, and 8 femurs had healed at 8 weeks (57%). No femoral defects in groups 2-4 demonstrated evidence of complete radiographic healing at any time point. Healing grades of femurs in group 1 were significantly greater than those from groups. 2-4 ($p<0.001$) at the 8- and 12-week time points (Table 3). There was no significant difference in radiographic scores between groups 2-4 ($p>0.05$) (Table 3). There was moderate interobserver agreement among the three reviewers who scored the radiographs (8-week kappa=0.60, 12-week kappa=0.61).

Figure 9:
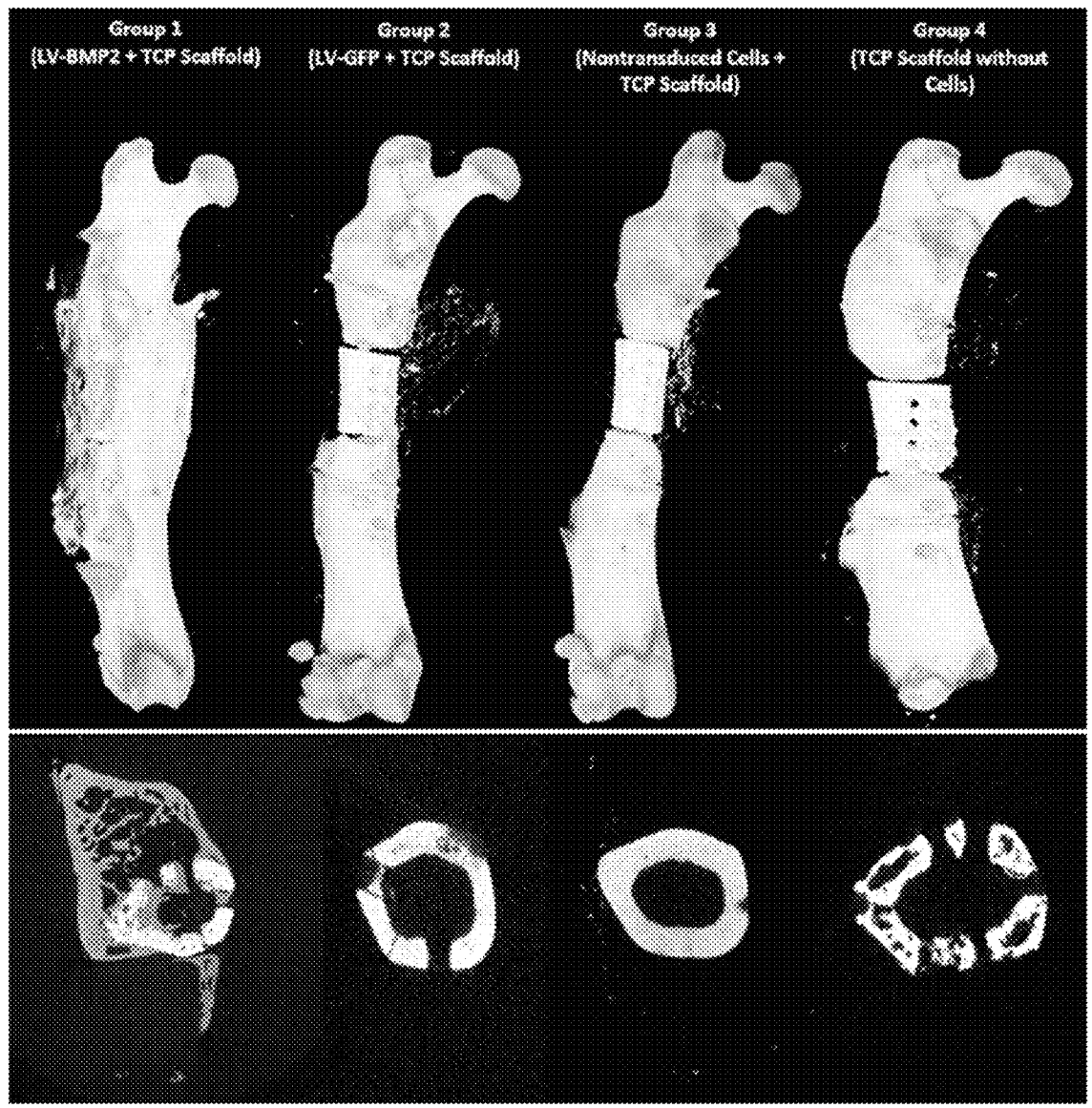
FIG. 9 depicts representative micro-CT scans with three-dimensional reconstructions (top) and axial images (bottom) obtained from groups 1-4 after specimen harvest. Group 1 demonstrated complete healing of the defect and on the axial image; circumferential bone can be seen surround the 3D printed TCP scaffold. No bone formed with the defect in groups 2-4.

Microcomputed Tomography: At the 12-week time point, Micro-CT confirmed complete healing of all 14 femurs in group 1. No bone formation was noted within the defect in groups 2-4. Micro-CT demonstrated approximately fivefold greater BVF in group 1 compared to groups 2-4 ($p<0.001$) (FIG. 9). There was no significant difference in BVF between groups 2-4 ($p>0.05$). The average BV/TV in group 1 was 25.33±9.05%, 6.03±3.34% in group 2, 4.10±0.54% in group 3, and 6.20±1.79% in group 4.

Figure 10:
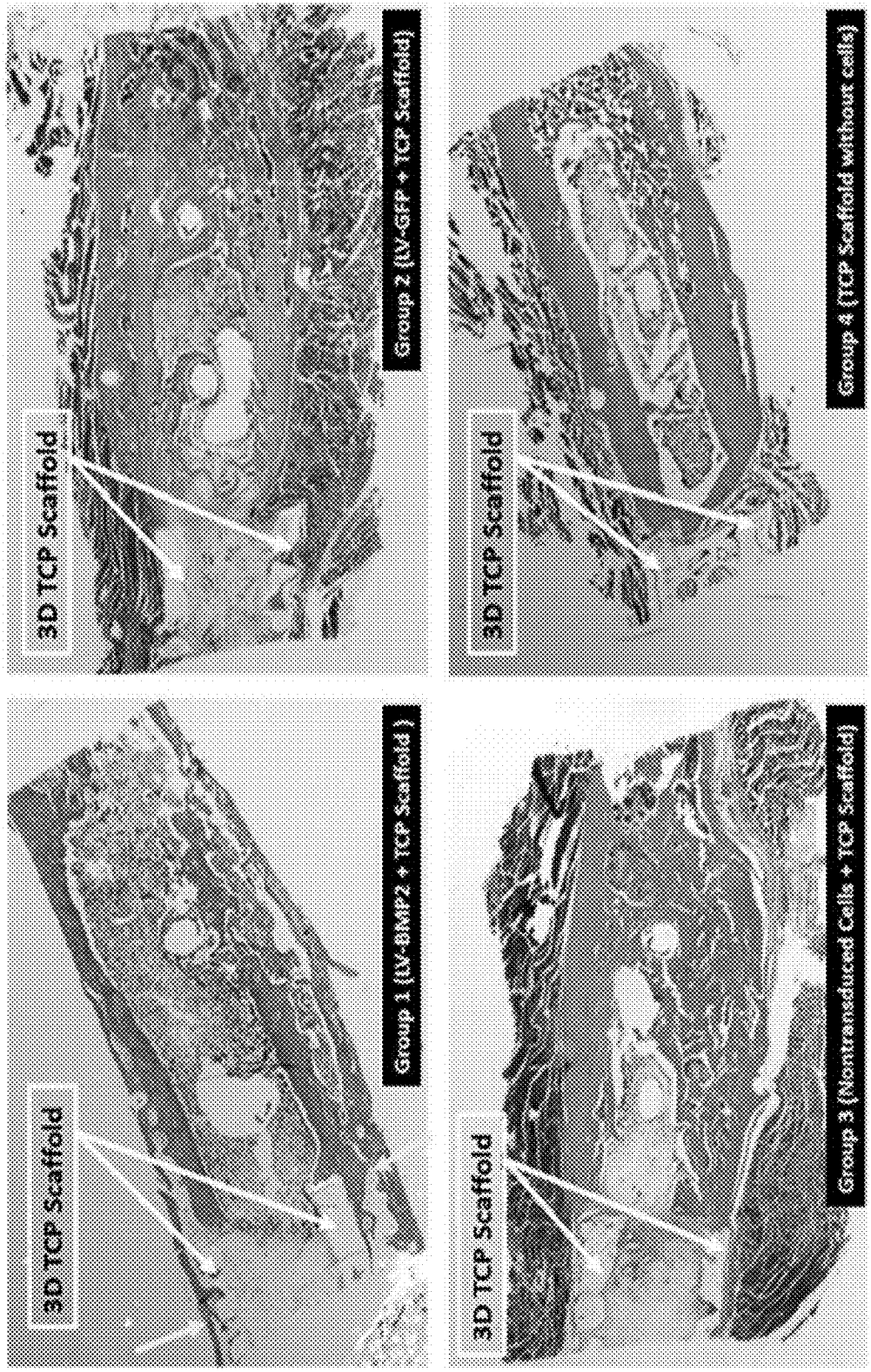
FIG. 10 depicts select longitudinal histological cuts of the proximal scaffold-defect interface from groups 1-4. The samples stained with Masson's trichrome stain. Group 1 demonstrated trabecular bone formation within the 3D printed TCP scaffold, uniting the scaffold to both ends of the defect. There is no notable bone groups 2-4, and the TCP scaffold is mostly surrounded by muscle.

Histology and Histomorphometry: The femurs from group 1 demonstrated substantial trabecular bone formation across the scaffold-bone interface both proximally and distally (FIG. 10). On cross-sectional samples, trabecular bone formed circumferentially around the entire 3D printed TCP scaffold in group 1. Groups 2-4 demonstrated minimal new bone formation at the scaffold-defect interface, and no bone formation surrounding the scaffold on cross-sectional imaging.

On H&E staining in one specimen from group 2 and a second from group 3, there was significant inflammatory cell infiltration and necrosis surrounding the pin sites. Both of these specimens had negative TRAP stains. TRAP staining around the proximal pin sites was positive in one specimen from group 2 and a second specimen from group 4; no significant inflammatory reaction in these two specimens was noted on H&E staining. No inflammatory reaction or TRAP positive specimens were noted in group 1.

Significant differences in bone formation between group 1 and groups 2-4 demonstrated on radiographs, micro-CT, and qualitative histology were confirmed with histomorphometric analysis. Total average bone volume induced by group 1 (BA/TA=0.134±0.056) was significantly greater than groups 2-4 ($p<0.05$). Average BA/TA was 0.052±0.022 in group 2, 0.056±0.043 in group 3, and 0.035±0.020 in group 4. There was no significant difference in BA/TA between groups 2-4 ($p>0.05$).

Biomechanics: The mean stiffness, total energy, peak torque, and peak displacement of the healed segmental defects from group 1 and the unoperated, contralateral femur are presented in Table 4. Stiffness between the healed defect and unoperated femur were similar ($p=0.863$). Total energy to failure, peak torque, and peak displacement were significantly greater in the unoperated femur ($p<0.001$). No defects in groups 2-4 demonstrated adequate bone formation and stability of the bone defect to undergo biomechanical testing.

Complications: There were no complications in the LV-BMP2+TCP scaffold group (group 1). One rat from group 3 died on postoperative day two likely secondary to complications from anesthesia; this rat was replaced. The proximal fixation in one rat in group 3 failed at 8 weeks and this rat was euthanized prior to the 12-week time point. In 3 rats (60%) in group 4, plain radiographs at 4, 8, and 12 weeks demonstrated migration of the TCP scaffold within the defect. This occurred because there was no bone healing in the defect. One rat from group 2 and one rat in group 4 were noted to have loose proximal pins at the time of limb harvest; these two rats had the positive TRAP staining on histology in the absence of significant inflammation, consistent with aseptic osteolysis. Two additional rats, one from group 2 and one from group 3, were noted to have purulent material at the loose proximal pin sites at the time of limb harvest. During the course of the study, the pins became loose and the superficial tip of the pins migrated and violated the epidermal layer, but this was not clearly evident during routine clinical inspection due to the rats' thick fur layer. The histologic sections of these two femurs revealed a significant inflammatory reaction but were TRAP negative.

TABLE 4

Biomechanics results of group 1 (LV-BMP2 + TCP scaffold)

| Outcome | Experimental Limb | Contralateral limb | p-value |
|---|---|---|---|
| Stiffness (nm/deg) | 0.06 +/− 0.02 | 0.06 +/− 0.01 | 0.863 |
| Total energy (nm deg) | 1.36 +/− 0.68 | 3.66 +/− 1.13 | <0.001 |
| Peak torque (nm) | 0.36 +/− 0.10 | 0.62 +/− 0.11 | <0.001 |
| Peak displacement (deg) | 8.36 +/− 1.40 | 12.4 +/− 2.42 | <0.001 |

Example 8

Growth Factor Transduced Cell-Loaded Ceramic Scaffold for Bone Generation and Repair The regional gene therapy strategy that is being developed includes the transduction of either adipose derived stem cells (ADSCs) or bone marrow cells that have been expanded in tissue culture.

The cells will be transduced with two-step transcriptional amplification (TSTA) lentiviral vector system containing the cDNA for BMP-2. The transduced cells will then be loaded onto a scaffold which has been implanted into the bone defect. The TSTA lentiviral vector system can use two different lentiviral vectors to express BMP-2. One of the vectors is the trans-activator vector (LV-RhMLV-Gal4) and the other vector is the BMP-2 containing vector under the control of a Gal4 responsive promoter including five Gal4 binding sites (LV-G5-BMP-2).

In previous studies different multiples of infection (MOI) have been evaluated for each vector to maximize BMP-2 production. In many of these studies the MOI for the trans-activator vector was 5 and a MOI of 25 for the BMP-2 vector (This has been delineated as 5/25). Recent studies have compared the BMP-2 production when the MOI was decreased to 3/3 for the trans-activator vector and BMP-2 vector respectively (See, Table 5). It is hypothesized that the higher MOI may be more toxic to the transduced cells.

TABLE 5

BMP-2 production at different MOIs
ADSCs: BMP-2 Production by Multiplicity
of Infection (MOI) – (ng/million cells)

|  | Statistics | Day 2 | Day 7 | Day 14 |
|---|---|---|---|---|
| ADSC 3/3 | Mean | 52.05 | 534.68 | 432.13 |
|  | N | 4 | 4 | 4 |
|  | Std. Deviation | 80.63 | 309.97 | 260.87 |
|  | Std. Error of the Mean | 40.31 | 154.98 | 130.435 |
| ADSC 5/25 | Mean | 60.83 | 138.93 | 29.17 |
|  | N | 3 | 3 | 3 |
|  | Std. Deviation | 18.22 | 47.37 | 17.10 |
|  | Std. Error of the Mean | 10.52 | 27.35 | 9.87 |

Figures 11A, 11B:
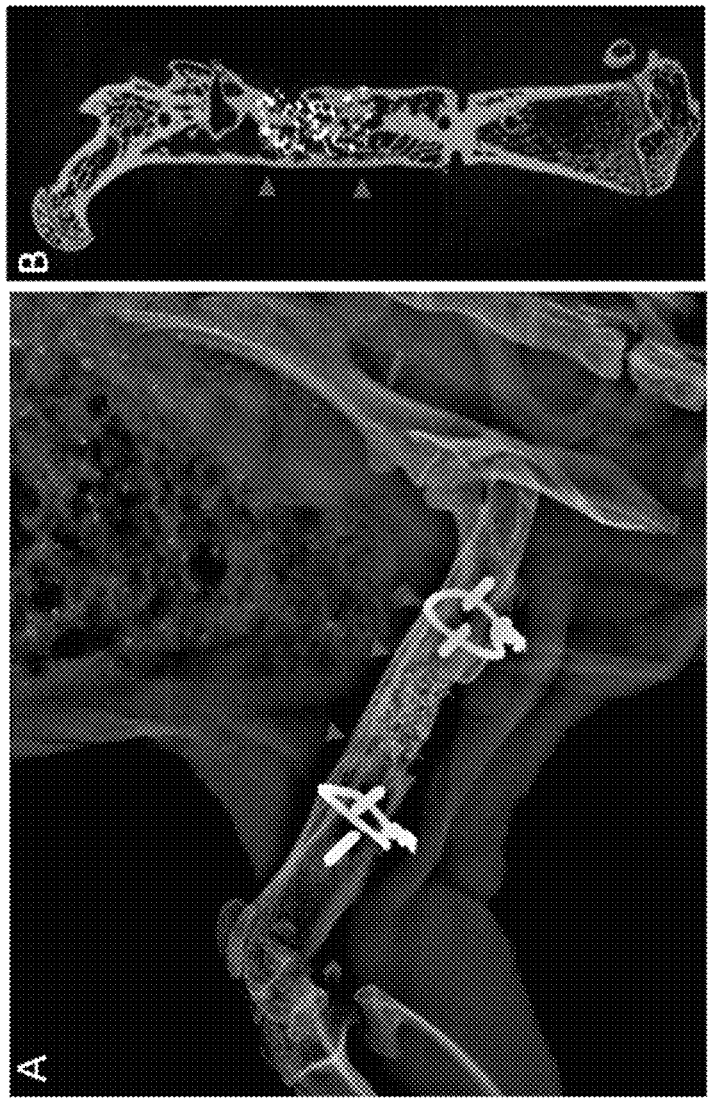
FIGS. 11A-11B depict x-ray and micro-computed tomography imaging of a rat femoral defect 12 weeks after treatment with human ADSCs transduced with a two-step transcriptional amplification (TSTA) lentiviral system overexpressing BMP-2.
Figure 12:
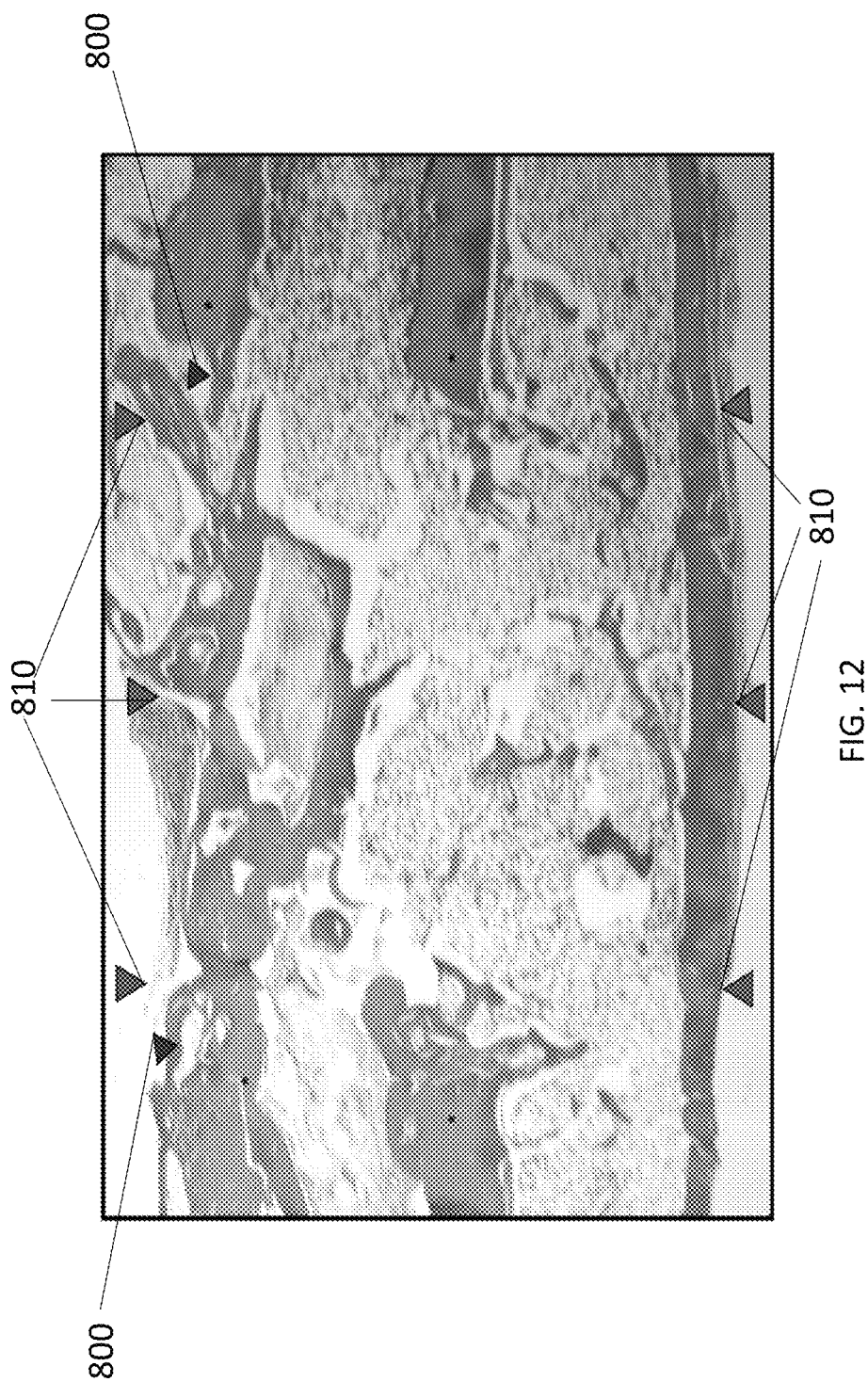
FIG. 12 depicts histological healing in a critically sized bone defect after 12 weeks. H&E stained longitudinal section revealed the bone defects 800 and the bridging bone that spanned the defect site 810. The asterisks (*) marks native bone.

A pilot study was performed assessing the bone defect healing capacity of transduced human ADSCs using a MOI 3/3 for the trans-activator and BMP-2 vectors. The transduced cells were loaded onto a compression resistant matrix that had been placed in a critically sized femoral defect in a nude rat. Twelve weeks after cell implantation the bone defect had healed with bridging of the bone defects as confirmed on plain radiographs and micro CT scan (FIGS. 11A-11B). Histological analysis also shows healing of defects 800 with bones that bridge the defect sites 810 (FIG. 12).

What is claimed is:

1. A method for repairing a bone defect of a patient, comprising:
providing a 3D model of a scaffold for bridging the bone defect;
providing a ceramic scaffold comprising calcium and phosphate based on the 3D model, wherein the ceramic scaffold comprises a tube-like structure that comprises an inner surface that matches the outer surface of a healthy bone,
wherein the ceramic scaffold is custom shaped to match morphology of healthy bone that surrounds the bone defect;
transducing any one or more of mesenchymal stem cells, bone marrow cells, fibroblasts, adipose-derived cells, umbilical cord cells, and muscle cells with a lentiviral vector system comprising (i) a trans-activator vector with a multiplicity of infection (MOI) of 3 and (ii) a vector encoding a growth factor essential for bone formation with a MOI of 3;
loading any one or more of mesenchymal stem cells, bone marrow cells, fibroblasts, adipose-derived cells, umbilical cord cells, and muscle cells, transduced with the lentiviral vector system, on the inner surface of the ceramic scaffold;
placing the ceramic scaffold into the bone defect of the patient; and
stabilizing the ceramic scaffold in the patient using a biocompatible metal plate or rod, until the bone defect is repaired.

2. The method of claim 1, further comprising forming the ceramic scaffold by 3D printing a calcium phosphate material.

3. The method of claim 1, wherein providing the 3D model comprises shaping the 3D model for causing the ceramic scaffold to match undamaged areas adjacent to the bone defect, so as to fit against the undamaged areas while spanning the bone defect.

4. The method of claim 1, wherein providing the ceramic scaffold comprises forming a plurality of holes in the range of 300 microns to 1000 microns in the ceramic scaffold.

5. The method of claim 1, wherein the growth factor essential for bone formation is bone morphogenetic protein 2.

6. The method of claim 1, wherein loading the any one or more of mesenchymal stem cells, bone marrow cells, fibroblasts, adipose-derived cells, umbilical cord cells, and muscle cells on the inner surface of the ceramic scaffold is performed before placing the ceramic scaffold into the bone defect of the patient.

7. The method of claim 6, further comprising performing a second loading step in which any one or more of the mesenchymal stem cells, bone marrow cells, fibroblasts, adipose-derived cells, umbilical cord cells, and muscle cells are loaded on the inner surface of the ceramic scaffold, wherein the second loading step is performed after placing the ceramic scaffold into the bone defect of the patient.

8. The method of claim 1, wherein placing the ceramic scaffold into the bone defect of the patient is performed before loading the any one or more of mesenchymal stem cells, bone marrow cells, fibroblasts, adipose-derived cells, umbilical cord cells, and muscle cells on the inner surface of the ceramic scaffold.

* * * * *